(12) United States Patent
Nigroni et al.

(10) Patent No.: US 7,250,025 B2
(45) Date of Patent: Jul. 31, 2007

(54) TIMING OF INTRA-AORTIC BALLOON PUMP THERAPY

(75) Inventors: Paul Nigroni, Wanaque, NJ (US); Brian Prais, Salisbury Mills, NY (US); Robert Freamon, Middletown, NY (US)

(73) Assignee: Datascope Investment Corp., Montvale, NJ (US)

( * ) Notice: Subject to any disclaimer, the term of this patent is extended or adjusted under 35 U.S.C. 154(b) by 356 days.

(21) Appl. No.: 10/928,534

(22) Filed: Aug. 27, 2004

(65) Prior Publication Data

US 2005/0148812 A1 Jul. 7, 2005

Related U.S. Application Data

(60) Provisional application No. 60/498,871, filed on Aug. 29, 2003.

(51) Int. Cl.
*A61N 1/362* (2006.01)

(52) U.S. Cl. ...................................................... 600/17
(58) Field of Classification Search ............. 607/16–18
See application file for complete search history.

(56) References Cited

U.S. PATENT DOCUMENTS

| | | | |
|---|---|---|---|
| 4,016,871 A | 4/1977 | Schiff | |
| 4,809,681 A | 3/1989 | Kantrowitz et al. | |
| 6,042,532 A * | 3/2000 | Freed et al. | 600/18 |
| 6,132,363 A | 10/2000 | Freed et al. | |
| 6,290,641 B1 * | 9/2001 | Nigroni et al. | 600/18 |
| 6,406,422 B1 * | 6/2002 | Landesberg | 600/17 |
| 6,511,412 B1 | 1/2003 | Freed et al. | |
| 6,679,829 B2 * | 1/2004 | Nigroni et al. | 600/18 |

* cited by examiner

*Primary Examiner*—Carl Layno
*Assistant Examiner*—Brian T. Gedeon
(74) *Attorney, Agent, or Firm*—Lerner, David, Littenberg, Krumholz & Mentlik, LLP

(57) ABSTRACT

In order to fully automate the inflation timing and deflation timing of an intra-aortic balloon pump, certain delays intrinsic in the system must be taken into account. A process for calculating these delays includes determining a nominal inflate command time, adding a dither time interval to the nominal inflate command time to obtain an actual inflate time, and determining a deflate command time. An inflation/deflation cycle is then processed in which the intra-aortic balloon pump is inflated at the actual inflate command time and deflated at the deflate command time. Blood pressure data is acquired from the patient during the inflation/deflation cycle, and is then analyzed to determine a realization time at which the effects of inflating the intra-aortic balloon are realized on the blood pressure waveform. From this the total delay time between the actual inflate command time and the realization time can be determined.

23 Claims, 11 Drawing Sheets

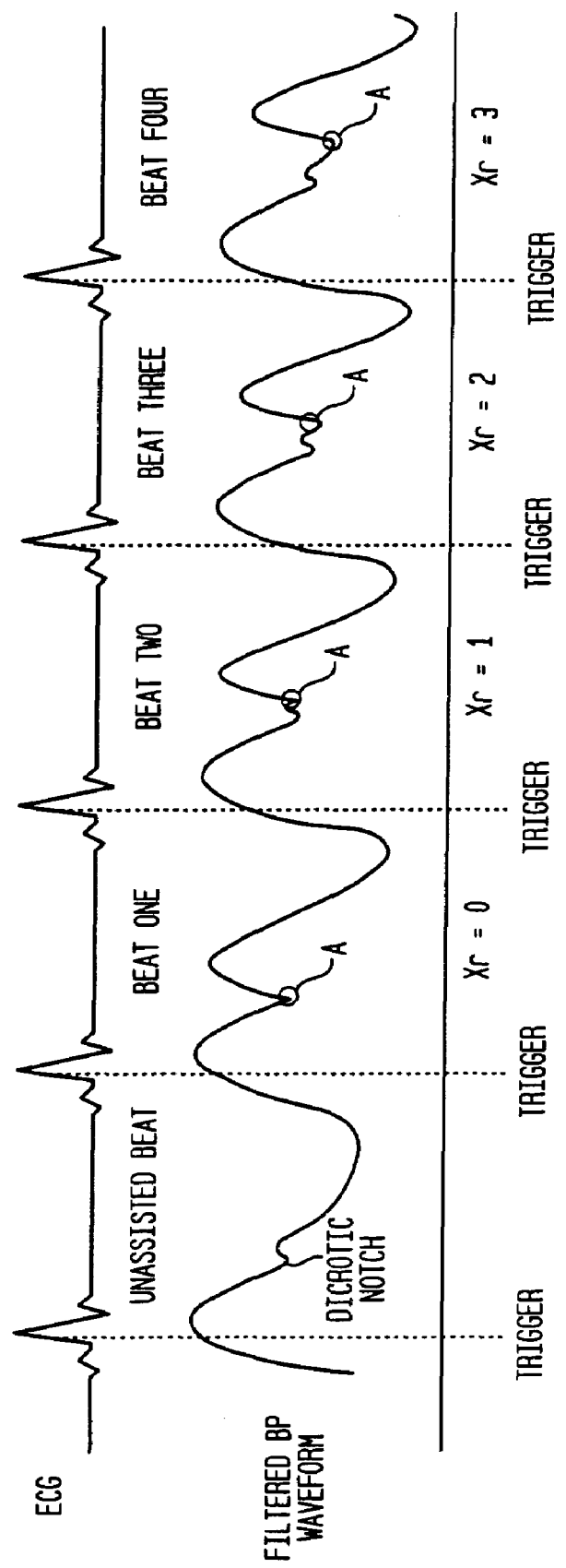

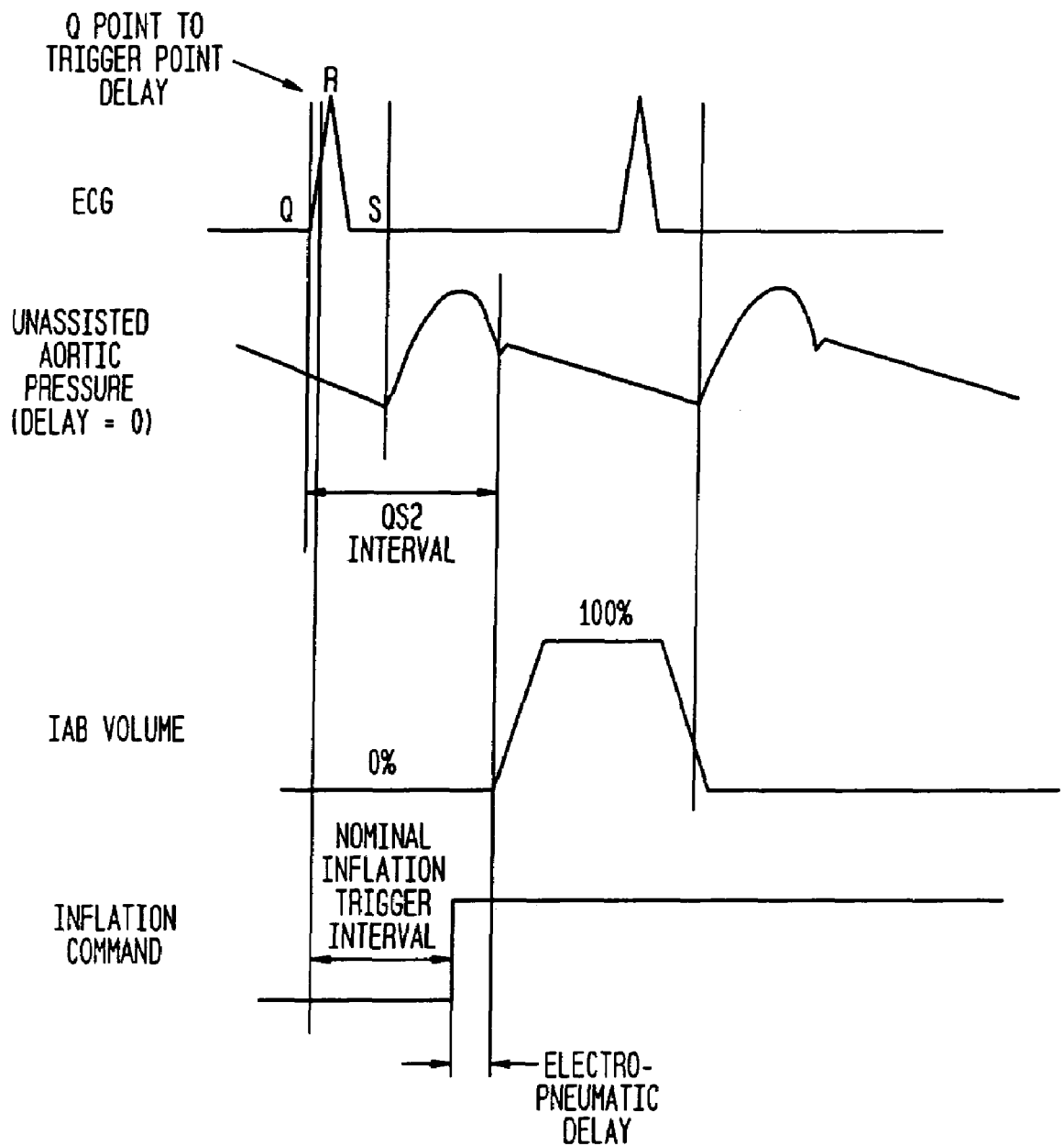

TIMING OF INTRA-AORTIC BALLOON PUMP THERAPY

CROSS-REFERENCE TO RELATED APPLICATIONS

This application claims the benefit of the filing date of U.S. Provisional Patent Application No. 60/498,871 filed Aug. 29, 2003, the disclosure of which is hereby incorporated herein by reference.

BACKGROUND OF THE INVENTION

The present invention relates generally to intra-aortic balloon pump therapy, and more particularly, to systems for inflating and deflating intra-aortic balloons. Still more particularly, the present invention relates to methods for use in setting the timing of the balloon inflation and deflation cycles in intra-aortic balloon-pump therapy.

Intra-aortic balloon pump (IABP) therapy is a form of temporary cardiac assist which is frequently prescribed for patients who have suffered a heart attack or some other form of heart failure. In such therapy, a thin balloon is inserted, typically through the femoral artery, into the patient's descending aorta. The balloon is connected through a series of thin tubes to a control apparatus which causes the balloon to inflate and deflate in time with the patient's heartbeat. The balloon therapy supports the left ventricle of the heart by increasing perfusion of the coronary arteries and by reducing left ventricular work. Coronary artery perfusion is increased by augmenting aortic pressure during the diastolic phase of the cardiac cycle. Left ventricular work is reduced by reducing aortic pressure at the end of diastole, i.e., at the onset of ventricular ejection.

The inflation/deflation apparatus supplies positive pressure for expanding the balloon during an inflation cycle and negative pressure for contracting the balloon during a deflation cycle. In a conventional apparatus, such as that shown schematically in FIG. 1, an intra-aortic balloon 10 is surgically inserted into a patient's descending aorta and is connected through a thin catheter 12 and a large diameter extender 14 to an isolator 18 divided by a pliant membrane 20 into a primary side 22 and a secondary side 24. The entire volume between membrane 20 and balloon 10 is filled with a shuttle gas, such as helium, supplied by a gas source 26. A positive pressure source 28 is connected through a solenoid valve 30 to the input or primary side 22 of isolator 18. Similarly, a negative pressure source 32 is connected through a solenoid valve 34 to the input or primary side 22 of isolator 18. The primary side 22 of isolator 18 is also connected through a solenoid valve 36 to a vent or exhaust port 38.

A central lumen 40 extends from an open end 42 protruding from the tip of balloon 10, through the balloon, catheter 12 and a Y junction 44, to a pressure transducer 46. A fluid, such as saline, fills lumen 40 so as to establish a continuous fluid column therein. As a result, the blood pressure in the descending aorta is transmitted by hydraulic coupling through the fluid column to pressure transducer 46 where it can be measured.

During an inflation cycle, solenoid valve 30 is opened to permit positive pressure from positive pressure source 28 to enter the primary side 22 of isolator 18. This positive pressure causes membrane 20 to move toward secondary side 24, thereby forcing the helium in the secondary side to travel toward and inflate balloon 10. For deflation, solenoid valve 30 is closed and solenoid valve 36 is opened briefly to vent the gas from primary side 22, after which valve 36 is closed. Solenoid valve 34 is then opened, whereupon negative pressure source 32 creates a negative pressure on the primary side 22 of isolator 18. This negative pressure pulls membrane 20 toward primary side 22, whereby the helium is drawn out from the balloon.

In order to achieve optimal therapeutic benefits from the use of an IABP system, the inflation and deflation cycles must be properly synchronized to the cardiac cycle. In particular, the balloon 10 must be inflated and deflated within the diastolic interval, when the left ventricle of the heart is inactive. The diastolic interval is determined based on the pressure waveform in the descending aorta, as transmitted from the tip of the balloon through lumen 40 to pressure transducer 46. The dicrotic notch on the waveform indicates the start of the diastolic interval (i.e., when the aortic valve has closed and left ventricular flow has ended), and the onset of systole defines the end of the diastolic interval (i.e., the beginning of left ventricular flow).

The effect of the IABP on aortic pressure is illustrated in the series of graphs shown in FIG. 2. For purposes of illustration, the figure shows time-aligned "assisted" and "unassisted" aortic pressure waveforms. The assisted waveform shows correct timing of balloon inflation and deflation with respect to the cardiac cycle (as represented by the electrocardiogram (ECG) waveform). Also shown in appropriate time alignment is the balloon volume reflecting the deflated and inflated conditions. Examples of early, late and correct timing for both inflation cycles and deflation cycles are shown in the graphs of FIG. 3.

To maintain correct timing on a continuous basis, the timing of the inflation and deflation cycles must be adjusted to accommodate changes in the patient's heart rate, rhythm and left ventricular contractility. In early IABP systems, this was accomplished manually through continuous operator monitoring of the IABP's aortic pressure waveform and adjustment of separate inflation and deflation timing controls based on certain cardiac events or landmarks. In current IABP systems, the maintenance of proper timing has been made semi-automatic. Inflate timing is initially set automatically based on the $Q$-$S_2$ interval determined from the previous R-R interval, and is adjusted manually by the operator based on the position of the augmentation curve relative to the dicrotic notch on the aortic pressure waveform. Thereafter, the proper inflate timing is estimated through the use of predefined regression algorithms. These algorithms adjust timing continuously, on a beat-to-beat basis, based on the R-R interval of the prior beat. Because changes in the patient's clinical status or medications can affect the contractility of the left ventricle, coronary artery blood flow, end diastolic volume and pressure, and heart rate, occasional operator intervention is needed to adapt the timing to these clinical changes or to audit and correct the estimation process. To provide a visual reference while setting timing, operators often set the IABP to assist (i.e., to inflate) every other heartbeat, rather than every heartbeat. By assisting every other heartbeat, operators are more easily able to visually detect timing errors by comparing assisted and unassisted pressure waveforms. Furthermore, the aortic pressure waveform during unassisted beats is free of artifacts that can be induced by balloon inflation, catheter movement, etc., thereby making the landmarks for proper inflation and deflation timing clearly visible.

Despite the improvements in operation achieved through partial automation of the inflation and deflation timing, IABP therapy still requires frequent adjustment and monitoring by an operator, and is subject to operator error both at startup and during periodic adjustment. It therefore would be desirable to fully automate IABP timing so as to eliminate the need for constant monitoring by an operator and avoid the potential for such operator errors.

Any attempt to fully automate IABP timing must take into consideration the requirement that IABP therapy be performed during the diastolic interval. More particularly, the balloon inflation cycle is preferably initiated so that augmentation of the aortic pressure begins at the start of the diastolic interval, i.e., at the dicrotic notch. Similarly, the balloon deflation cycle is preferably initiated so that full deflation is reached at the end of the diastolic interval, i.e., at the beginning of systole. If the commands to inflate or deflate the balloon are issued at the time these cardiac events are detected, the resultant timing would be persistently late. This is a consequence of the delays that are inherent in IABP systems. For example, if the balloon inflation cycle is initiated at the time the dicrotic notch is detected, the intrinsic time delays in the IABP system would result in a late augmentation of the aortic blood pressure. Similarly, if the balloon deflation cycle is initiated at the time the end of the diastolic interval is detected, the intrinsic time delays would cause complete deflation of the balloon to occur too late. Although the use of earlier surrogates to predict the occurrence of these cardiac events has been considered, such surrogates have generally proven to be unreliable.

The time delays intrinsic to IABP systems consist of several components. One source of delay is the electro-pneumatic delay associated with the activation of valves, the pressurization of pneumatic volumes and the movement of the shuttle gas to begin inflation or deflation of the balloon, all of which follow a balloon inflation or deflation command. Another source of delay is the time for the shuttle gas to move substantially into (i.e., inflate) or out from (i.e., deflate) the balloon. Yet a further delay is the time from the closing of the aortic valve until the aortic pressure change resulting from that event (i.e., the dicrotic notch) is propagated to the blood pressure monitoring site. For central lumen monitoring, such as depicted in FIG. 1, the monitoring site is the tip of the balloon 10. Still another source of delay is the time it takes the pressure signal to propagate from the monitoring site until its conversion into an electrical signal. For central lumen monitoring, this is the time for the pressure signal to propagate from the tip of balloon 10 to pressure transducer 46.

These pressure delays can best be understood by reference to FIG. 4. This figure shows an ECG waveform followed by a waveform indicating the blood pressure as it exists in the descending aorta. Because of the delays caused by the propagation of blood pressure changes from the aortic valve to the pressure monitoring site and from the monitoring site until its conversion into an electrical signal, the blood pressure waveform as displayed on the console of an IABP system will lag in time from the blood pressure in the descending aorta. This lag in time can be seen in the perceived time shift in the third waveform shown in FIG. 4 which is the blood pressure as measured by transducer 46.

The electro-pneumatic delay is dominated by the contribution of the solenoid activated pneumatic valve which opens a pathway between the balloon and a pressure source during inflation, and between the balloon and a vacuum source during deflation. The excursion of this valve is highly repeatable, such that the delay associated with the valve movement is repeatable from patient to patient and cycle to cycle of the IABP. The time to transfer the shuttle gas into and out from the balloon also varies little from cycle to cycle. Accordingly, these two delay criteria may be considered constants.

The delays associated with propagating changes in aortic pressure from the aortic valve to the blood pressure monitoring site and with propagating pressure signals from the monitoring site until they are converted into electrical signals, however, are highly variable. Factors which impact these pressure delays include the location of the balloon, the location of the blood pressure monitoring site, the quality of the hydraulic coupling, and electronic monitoring considerations. There also may be other variable or constant intrinsic delays in an IABP system. For example, while the electro-pneumatic delay and the shuttle gas transfer time may be considered constants, their values are only estimates based on collected data. Errors in these estimates may result in actual delays that are greater than or less than the estimated values. The total amount of intrinsic delay in an IABP system regardless of its source, less any estimated constants ascribed to specified events, such as the electro-pneumatic delay and shuttle gas transfer time, are referred to collectively herein as the arterial pressure delay (APD).

When an operator adjusts IABP inflation and/or deflation timing based on differences between the appearance of the augmentation curve on the pressure waveform and the appearance of the dicrotic notch, what he is implicitly doing is adjusting the timing to account for the APD. That is, the operator is making the timing sooner or later to account for intrinsic delays in the IABP system so that the inflation and deflation commands will be issued at the appropriate times to enable the effects of inflation and deflation to be realized at the proper time relative to cardiac events.

As the optimal timing of IABP therapy requires a knowledge of the cumulative intrinsic delays, and as the highly repeatable delays are known, there exists a need for a method for automatically determining the APD for each patient. Preferably, such method will enable the APD to be determined accurately and quickly so that the IABP timing can be optimally set not only on a patient by patient basis at the initiation of therapy, but also at periodic intervals during therapy to assure that the timing remains optimal despite changes in the patient's cardiac performance.

SUMMARY OF THE INVENTION

The present invention addresses these needs.

One embodiment of the present invention provides a method of determining time delays in an intra-aortic balloon pump system between the occurrence of a blood pressure in a patient at a point in time and the display of a pressure value corresponding to the blood pressure in the patient at the point in time on a blood pressure waveform, the intra-aortic balloon pump system including an inflatable chamber, the method including (a) determining a nominal time to issue an inflate command for inflating the inflatable chamber based on an ECG waveform of the patient's heartbeat; (b) adding a dither time interval to the nominal inflate command time to obtain an actual inflate command time; (c) determining a time to issue a deflate command for deflating the inflatable chamber based on the blood pressure waveform; (d) processing an inflation/deflation cycle in which the inflatable chamber is inflated at the actual inflate command time and deflated at the deflate command time; (e) acquiring blood pressure data from the patient during the inflation/deflation cycle; (f) analyzing the acquired blood pressure data to determine a realization time at which the effects of inflating the inflatable chamber are realized on the blood pressure waveform; and (g) determining a delay time between the actual inflate command time and the realization time.

Another embodiment of the present invention provides an apparatus for assisting the cardiac function of a patient. The apparatus includes an inflatable chamber operably positionable with respect to an aorta of the patient; a catheter connectable in fluid communication with the inflatable chamber; and a drive unit connectable to the catheter for selectively inflating and deflating the inflatable chamber in accordance with a control program, the control program including a process of determining time delays in the apparatus between the occurrence of a blood pressure in the patient at a point in time and the display of a pressure value corresponding to the blood pressure in the patient at the point in time on a blood pressure waveform. The process includes (a) determining a nominal time to issue an inflate command for inflating the inflatable chamber based on an ECG waveform of the patient's heartbeat; (b) adding a dither time interval to the nominal inflate command time to obtain an actual inflate command time; (c) determining a time to issue a deflate command for deflating the inflatable chamber based on the blood pressure waveform; (d) processing an inflation/deflation cycle in which the inflatable chamber is inflated at the actual inflate command time and deflated at the deflate command time; (e) acquiring blood pressure data from the patient during the inflation/deflation cycle; (f) analyzing the acquired blood pressure data to determine a realization time at which the effects of inflating the inflatable chamber are realized on the blood pressure waveform; and (g) determining a delay time between the actual inflate command time and the realization time.

Yet a further embodiment of the present invention provides a method of assisting the cardiac function of a patient. The method includes (a) inserting an inflatable chamber in a selected position with respect to an aorta of the patient; (b) determining a nominal time to issue an inflate command for inflating the inflatable chamber based on an ECG waveform of the patient's heartbeat; (c) adding a dither time interval to the nominal inflate command time to obtain an actual inflate command time; (d) determining a time to issue a deflate command for deflating the inflatable chamber based on a pressure waveform corresponding to the blood pressure in the patient; (e) processing an inflation/deflation cycle in which the inflatable chamber is inflated at the actual inflate command time and deflated at the deflate command time; (f) acquiring blood pressure data from the patient during the inflation/deflation cycle; (g) analyzing the acquired blood pressure data to determine a realization time in which the effects of inflating the inflatable chamber are realized on the blood pressure waveform; (h) determining a delay time between the actual inflate command time and the realization time; (i) adjusting the nominal inflate command time by the delay time to obtain a modified inflate command time; and (j) repeatedly inflating the inflatable chamber at the modified inflate command time and deflating the inflatable chamber at the deflate command time.

In each of the foregoing embodiments of the invention, for a selected heartbeat, the dither time interval may be based upon an average of the R-R interval over a predetermined number of the patient's heartbeats immediately preceding the selected heartbeat. Preferably, the dither time interval is proportional to an average of the R-R interval over a predetermined number of the patient's heartbeats immediately preceding the selected heartbeat.

The process for determining time delays may further include the step of determining a duration interval between the actual inflate command time and the deflate command time, and if the duration interval is less than a predetermined time interval, the deflate command time may be adjusted so that the duration interval is at least as large as the predetermined time interval.

The process for determining time delays may be repeated for a plurality of inflation/deflation cycles. In each inflation/deflation cycle the dither time interval added to the nominal inflate command time may be different from the dither time interval added to the nominal inflate command time in other inflation/deflation cycles. In such event, the analyzing step may include averaging the blood pressure data acquired during the plurality of inflation/deflation cycles on a time-aligned point-by-point time basis to obtain an ensemble average, and analyzing the ensemble average to determine an average realization time at which the effects of inflating the inflatable chamber are realized on the blood pressure waveform. The step of determining the delay time may include determining a time-aligned inflate command time based on the actual inflate command time for each of the inflation/deflation cycles and determining a time interval between the time-aligned inflate command time and the average realization time.

For each inflation/deflation cycle, the dither time interval added to the nominal inflate command time may be greater than the dither time interval added to the nominal inflate command time in an immediately preceding inflation/deflation cycle.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 6 is a series of graphs showing the process of the present invention for determining the APD as represented on the aortic blood pressure curve and in relationship to the cardiac cycle;

FIG. 7 is a series of graphs showing the timing of the balloon inflation command in relation to the ECG waveform, aortic pressure curve, and balloon volume;

DETAILED DESCRIPTION

Figure 1:
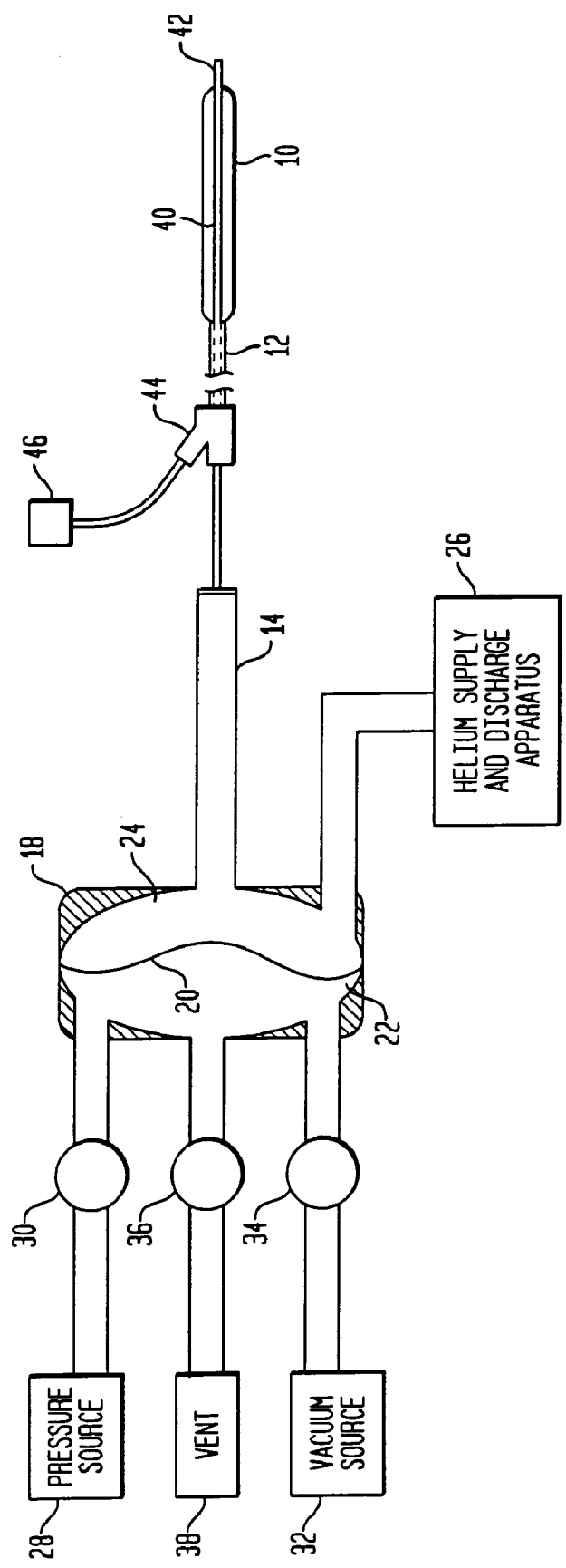
FIG. 1 is a highly schematic view showing a conventional system for inflating and deflating an intra-aortic balloon.
Figure 2:
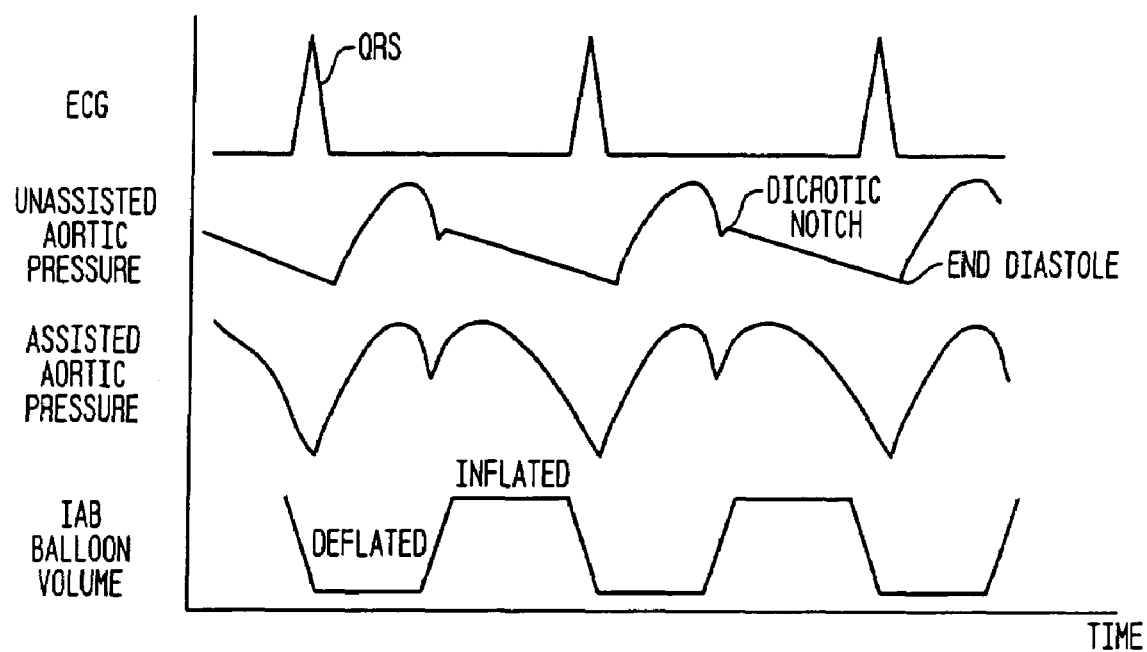
FIG. 2 is a series of graphs showing the relationship among the ECG waveform, unassisted aortic pressure, assisted aortic pressure and the volume in the intra-aortic balloon during inflation and deflation cycles.
Figure 3:
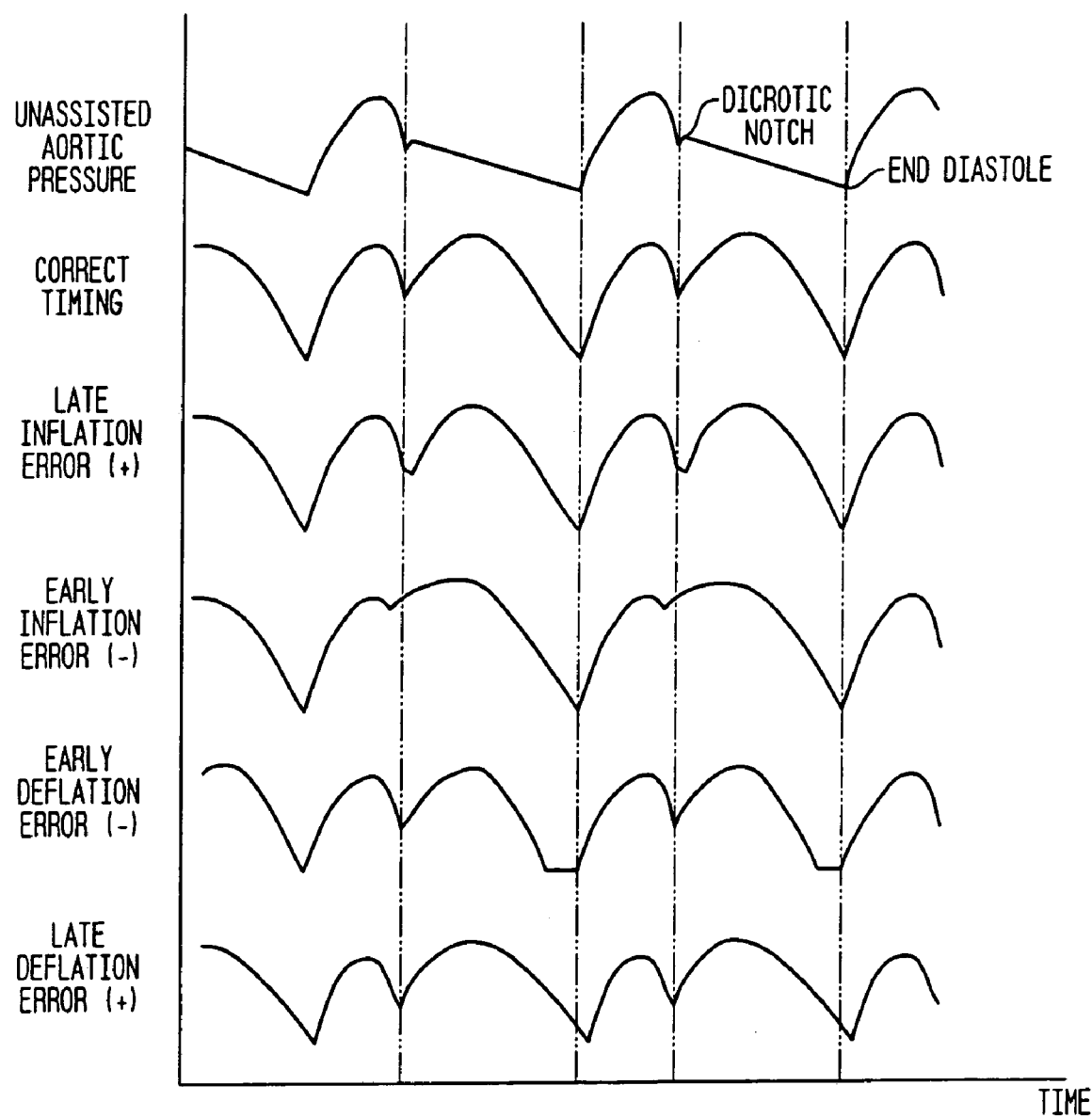
FIG. 3 is a series of graphs showing the relationship between unassisted aortic pressure and assisted aortic pressure with and without correct inflation/deflation timing.
Figure 4:
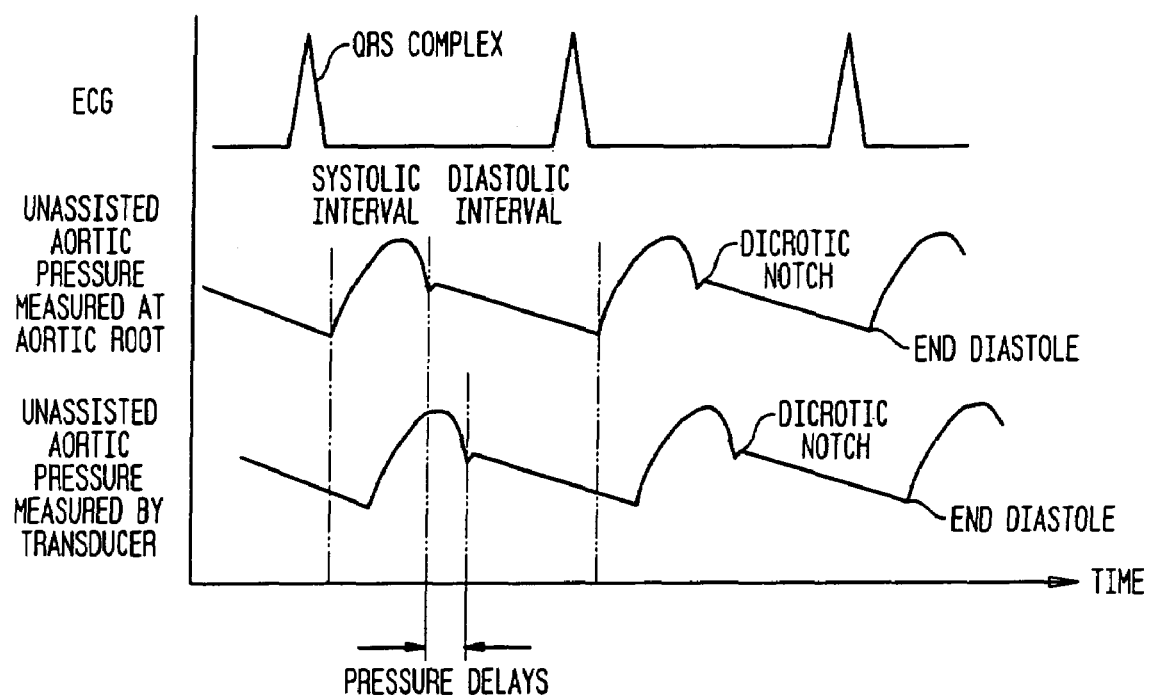
FIG. 4 is a series of graphs showing the relationship among the ECG waveform and the unassisted aortic pressure as it exists real time in the descending aorta and as it is converted into an electrical signal.

The present invention relates to a method for controlling the timing of a cardiac assist device in a patient in order to optimize diastolic augmentation. Various diastolic augmentation systems and devices are currently known. For example, the present invention may be used to control inflation and deflation of a balloon that is permanently or temporarily disposed in the descending aorta of a patient. Such devices, including that shown schematically in FIG. 1, are well known in the art, and therefore a detailed description of their structure and operation is omitted.

During IABP therapy, balloon inflation occurs in real time. However, the effect of inflation as shown on the aortic blood pressure waveform is not seen in real time. Rather, there is a delay between the time at which the balloon inflation command is issued and the time at which the pressure augmentation resulting from balloon inflation is seen on the aortic blood pressure waveform. This delay consists of the electro-pneumatic delay of the IABP system and the APD. (For inflation timing, the time for the balloon to fully inflate is not critical since the effects on blood pressure are initially seen almost immediately as inflation begins, not when inflation has been substantially completed). In the deflation cycle, there is a similar delay between the time at which the balloon deflation command is issued and the time at which the balloon is substantially deflated (i.e., about 90% of the shuttle gas has been removed from the balloon). This delay also consists of the electro-pneumatic delay of the IABP system and the APD, as well as the time it takes the shuttle gas to leave the balloon.

The electro-pneumatic delay is primarily dependent upon the configuration of the IABP system. Accordingly, for a particular IABP system, the electro-pneumatic delay is generally repeatable from one patient to another and from one inflation/deflation cycle to another, and therefore may be considered a constant. The APD, on the other hand, is dependent upon the balloon placement, hydraulic coupling considerations and other factors, and therefore varies from patient to patient and possibly during IABP therapy.

Because of these intrinsic delays in IABP therapy, in order for aortic blood pressure augmentation to begin at the dicrotic notch of the aortic blood pressure waveform, the command to inflate the balloon must be given at some time prior to the occurrence of the dicrotic notch. This time consists of the sum of the electro-pneumatic delay and the APD. Similarly, in order for the balloon to be substantially deflated at the end of diastole, the command to deflate the balloon must be given at some time prior to the end of the diastolic period consisting of the electro-pneumatic delay, the APD and the time to remove the shuttle gas from the balloon. Since the electro-pneumatic delay and the time to remove the shuttle gas from the balloon are known for any IABP system, the present invention provides a process for automatically determining the APD, thereby enabling the times for issuing the balloon inflation and deflation commands to be set automatically for each patient.

The APD for any particular IABP therapy session will depend in part upon the source of the blood pressure signal. In central lumen monitoring, as shown in FIG. 1, the blood pressure signal is propagated through a fluid-filled lumen from the descending aorta to a pressure transducer. When central lumen monitoring is not available, arterial blood pressure may be monitored at other sites, such as the patient's radial artery. In this case, the pressure is also monitored using hydraulically coupled pressure transducers. The time delay (APD) associated with this measurement site greatly exceeds that of central lumen monitoring due to its greater distance from the aortic valve. In still other arrangements, high level blood pressure signals obtained from an external monitoring source may be fed into the IABP system. An even longer APD is expected in such arrangements not only because of the distance of the measurement site from the aortic valve, but also because of the time delays associated with processing and transmitting the signals. Although the expected APD is different depending on which arrangement is used to acquire the blood pressure signals, the method for determining the APD is the same regardless of the signal source.

The following description assumes that the IABP system is in an assist mode in which the balloon is being inflated and deflated to augment aortic pressure during diastole. The description also assumes that the IABP is set to inflate/deflate the balloon (i.e., pump) on each heartbeat. While there are situations in which the IABP may not be set to pump on each heartbeat (for example, it may be set to pump on every other heartbeat so that the assisted and unassisted pressure curves can be compared), one skilled in the art would recognize how to modify the process to accommodate those situations. Finally, the following describes a process for determining the APD when an ECG trigger is used, that is, wherein balloon inflation is initiated based upon the R-R interval of the previous heartbeat.

After the balloon has been inserted into the patient's descending aorta and all appropriate sensors and leads have been connected to the patient, the apparatus is subjected to a conventional purge/fill routine. In such routine, a strong vacuum is exerted on the balloon to purge the air therefrom. The balloon is then filled with a fixed volume of shuttle gas, typically helium. This process is then repeated to ensure a high concentration of helium in the shuttle gas used to inflate the balloon.

Once the purge/fill routine has been completed, the IABP software commences the process for determining the APD with a subroutine to establish the balloon inflation and deflation trigger intervals. Referring to the flowchart of FIG. 5A, the first step of the subroutine, shown at step 100, sets a sequential failure counter j to zero and an APD result counter p to one. Subsequently, at step 102, an inflate/deflate counter Xr, an assist duration counter z, and a dither amount Yo (explained below) are all set to zero. The process then proceeds to step 104 at which the nominal inflation trigger interval is determined. As used herein in connection with an ECG trigger process, "nominal inflation trigger interval" refers to the time from the trigger point on the ECG waveform until the balloon inflation command is given, taking into account electro-pneumatic delay, but not APD. The nominal inflation trigger interval for the first cycle is determined in a conventional fashion based on the following regression equation which uses the R-R interval to predict the Q-S$_2$ interval:

$$t_Q(msec) = m*(t_{r\text{-}r\_inf}) + B$$

where:
- $t_Q$ is the Q-S$_2$ interval, i.e., the time interval between the Q point on the ECG waveform and the dicrotic notch on the aortic blood pressure waveform;
- $t_{r\text{-}r\_inf}$ is the R-R interval of the previous heartbeat; and
- m is the slope of the regression curve and B is the Q-S$_2$ intercept for the regression curve. Both of these values are determined from large quantities of data over many patients. Typically, m has a value of from about 0.21 to about 0.25,and B has a value of from about 165 msec to about 255 msec.

The nominal inflation trigger interval is determined from the Q-S$_2$ interval using the following equation to account for certain delays:

$$t_i(msec) = t_Q - D_{rtrig} - D_{ep\_inf}$$

where:

t$_i$ is the nominal inflation trigger interval;

D$_{rtrig}$ is the time interval between the Q point on the ECG waveform and the trigger point, and is assumed to be a constant of 30 msec. This interval, often called "trigger delay", is the time required for the amplitude of the QRS complex to exceed the trigger threshold. High trigger thresholds reduce trigger error but increase trigger delay. A typical trigger threshold is 50% of the amplitude of the QRS complex; and D$_{ep\_inf}$ is the electro-pneumatic delay, and is assumed to be a constant of 28 msec.

The relationship of the Q-S$_2$ interval, nominal inflation trigger interval and electro-pneumatic delay to the trigger point is shown graphically in FIG. 7.

Once the nominal inflation trigger interval has been determined for the first cycle, the process proceeds to step 106 at which an amount of dither is calculated from the equation:

$$Yo = Xr/16 * t_{r-r\_inf\_avg}$$

where:

Xr is a number representing the inflation/deflation cycle for which the inflation and deflation trigger intervals are being determined. For the first inflation/deflation cycle, Xr=0; for the second inflation/deflation cycle, Xr=1; etc.; and t$_{r-r\_inf\_avg}$ is the average R-R interval over the previous eight heartbeats or some other fixed number of heartbeats.

As used herein, the term "dither" refers to the deliberate movement of the inflation trigger interval in time increments on the blood pressure curve. The purpose of this dithering process is to isolate the inflation effect from noise and physiological events such as the dicrotic notch, end diastole, etc. which appear on the blood pressure curve, thereby assuring that such physiological effects are not mistaken for the onset of augmentation. Since Xr is zero during this first inflation/deflation cycle, the amount of dither for this first cycle is also zero.

At step 108, the current amount of dither Yo is added to the nominal inflation trigger interval t$_i$ to yield the actual inflation trigger interval for the first inflation cycle. The process then proceeds to step 110.

Figure 8:
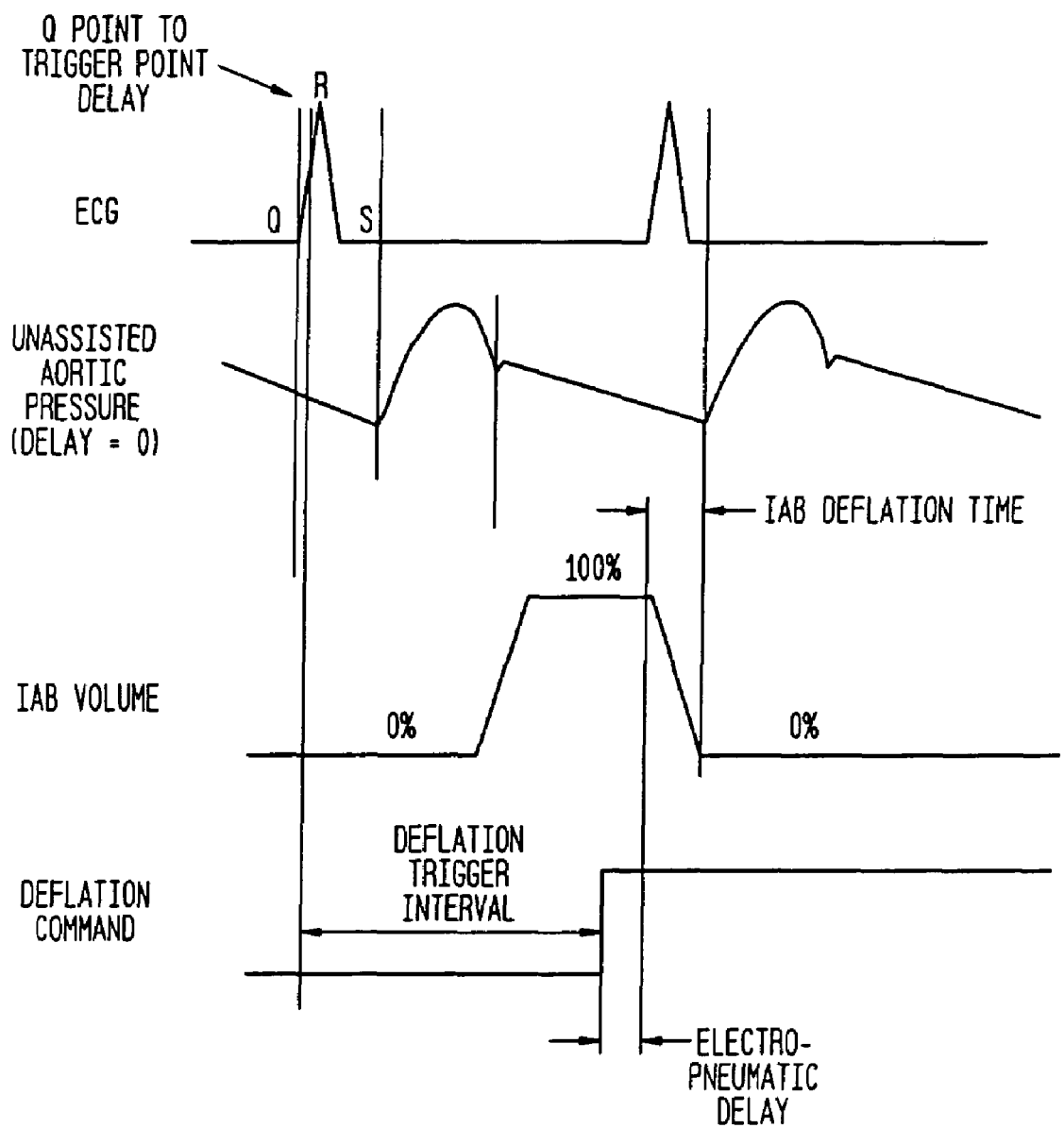
FIG. 8 is a series of graphs showing the timing of the balloon deflation command in relation to the ECG waveform, aortic pressure curve, and balloon volume.

At step 110, the deflation trigger interval is set. As used herein with respect to an ECG trigger process, "deflation trigger interval" refers to the time from the trigger point on an ECG waveform until the balloon deflation command is given. The deflation trigger interval may be determined in a conventional fashion by applying well-known analytical techniques to the pressure waveform based on an average of a fixed number of previous R-R intervals to determine the endpoint of diastole. From that point, certain constants are subtracted which represent the electro-pneumatic delay, the time to reach about 90% of balloon deflation, and a current estimate of the APD. If a current estimate of the APD has not been generated, a default value of 40 msec may be used as a typical expected value for APD as observed through experimentation using central lumen monitoring. The relationship of the deflation trigger interval, electro-pneumatic delay and end diastole to the trigger point is shown graphically in FIG. 8.

The process then proceeds to step 112 in which a determination is made of whether the duration of balloon assist as determined from the inflation and deflation set points (i.e., the time between the issuance of the balloon inflate command as determined from the actual inflation trigger interval and the issuance of the balloon deflate command as determined from the deflate trigger interval) will be greater than or equal to 72 msec. The 72 msec time duration is not critical, but is a value that will assure a minimum assist period from which a measurable inflation effect may be obtained. Thus, depending on the circumstances, thresholds of less than or greater than 72 msec may be used as long as a measurable inflation effect is obtainable.

If the time interval evaluated at step 112 will be less than 72 msec, the process proceeds to step 114 at which the deflation trigger interval is adjusted such that the duration of balloon assist will be 72 msec. The process then proceeds to step 116. If, on the other hand, step 112 determines that the duration of balloon assist will be greater than or equal to 72 msec, step 114 is omitted and the process proceeds to step 116.

At step 116, two commands are issued at a time from the trigger point equal to the actual inflation trigger interval determined in step 108. An inflate command causes valve 30 to open to commence inflation of the balloon. The second command begins collection of digitized blood pressure signal data. The blood pressure signals are sampled at a constant rate of about 250 Hz for a fixed interval (approximately 300 msec) so that about 75 data points on the blood pressure waveform are collected. The collected data is preferably digitally filtered through an 11 Hz IIR filter and a 60 Hz FIR filter to suppress noise and signal artifacts. After a period of time sufficient to inflate balloon 10, valve 30 is closed.

Continuing to step 118, a deflate command is issued to open valve 34 to commence deflation of the balloon. The deflate command is issued prior to end diastole at a time from the trigger point equal to the deflation trigger interval as determined in step 110 (or as set in step 114). After a period of time sufficient to deflate balloon 10, valve 34 is closed. The process then proceeds to step 119 in which the collection of blood pressure signal data is terminated. Although the termination of data collection is based upon an elapsed time and not upon any particular cardiac or balloon event, the collection time is set sufficiently long as to encompass the balloon inflation effects.

Following the initial inflation/deflation cycle, the process proceeds to step 120 at which a determination is made as to whether balloon assist actually lasted for a period of 72 msec or more. As will be appreciated, certain patients undergoing IABP therapy may exhibit very erratic heartbeats. Accordingly, balloon assist may have lasted for less than the scheduled time, for example, if a premature R wave was detected and a command to automatically deflate the balloon was issued before the scheduled deflate time. Automatic deflation assures that the balloon is not inflated during the ventricular ejection of the heart. If an assist duration greater than or equal to 72 msec is observed, the process proceeds to step 121 at which the assist duration counter z is incremented by one. The process then proceeds to step 122. On the other hand, if an assist duration of less than 72 msec is observed, the process advances directly to step 122. At step 122, a determination is made as to whether Xr is equal to three. If Xr equals three, the process proceeds to step 126 described below. On the other hand, if Xr does not equal three, the process proceeds to step 124 at which counter Xr is incremented by one.

From step 124, the process returns to step 104 to determine the nominal inflation trigger interval for the next successive cycle. This determination uses the same algorithms as described in step 104 above, but uses the R-R interval of the previous heartbeat to determine the $Q-S_2$ interval from the regression formula. Based on the nominal inflation trigger interval, the actual inflation trigger interval for the second inflation cycle can be determined by adding the dither amount calculated in step 106. Since Xr for the second inflation cycle is equal to one, the dither amount calculated in step 106 will equal $1/16 * t_{r-r\_inf\_avg}$ or 1/16 of the average R-R interval for the previous eight heartbeats. In determining the average R-R interval, the most recent R-R interval is added to the average calculation and the earliest R-R interval from the prior average is deleted from the calculation.

When the second actual inflation trigger interval has been determined at step 108 and the second deflation trigger interval has been determined at steps 110-114, the process again proceeds to step 116 at which balloon inflation and data collection are started. Subsequently, the balloon is deflated at step 118, pressure data acquisition is terminated at step 119, and an evaluation of the actual duration of balloon assist is made at steps 120 and 121. At step 122, if the counter Xr is still not equal to three, Xr is again incremented by one at step 124 and the process returns to step 104 and proceeds to determine the actual inflation trigger interval and the deflation trigger interval for the next cycle.

Steps 104 through 124 may be repeated for four successive inflation/deflation cycles, in each of which the dither added to the nominal inflation trigger interval is increased by 1/16 of the previous average R-R interval. Hence, the dither for the first inflation cycle is zero, the dither for the second inflation cycle is $1/16 * t_{r-r\_inf\_avg}$, the dither for the third inflation cycle is $1/8 * t_{r-r\_inf\_avg}$, and the dither for the fourth inflation cycle is $3/16 * t_{r-r\_inf\_avg}$. In the fourth cycle, Xr will equal three. Accordingly, in the fourth cycle, the process proceeds from step 122 to step 126.

The effect of the dithering process can be seen in the blood pressure waveform shown in FIG. 6. FIG. 6 shows the pressure waveform for an unassisted heartbeat, followed by the pressure waveform for four assisted heartbeats to which increasing amounts of dither have been applied. In the first assisted heartbeat (Xr=0), no dither is added to the inflation timing. Point A is the time at which the effects of balloon inflation (i.e., a rise in blood pressure) are first realized. Although point A as shown in FIG. 6 coincides with or precedes the dicrotic notch for the first heartbeat, that is not essential, and point A can occur anywhere in the pressure waveform. Using the process described above to determine the inflation command time, point A preferably occurs at or after the dicrotic notch. In the second assisted heartbeat (Xr=1), an amount of dither equal to $1/16 * t_{r-r\_inf\_avg}$ is added to the inflation timing, moving point A later in time, and clearly subsequent to the dicrotic notch. This enables the location of point A to be more clearly evaluated without interference from the physiological effects at the dicrotic notch. In the third assisted heartbeat (Xr=2), the amount of dither is increased to $1/8 * t_{r-r\_inf\_avg}$, moving point A to a later point on the diastolic runoff. In the fourth assisted heartbeat (Xr=3), the addition of a dither amount of $3/16 * t_{r-r\_inf\_avg}$ moves point A farther along the diastolic runoff and away from the dicrotic notch. Hence, it can be seen that greater amounts of dither have the effect of isolating the effects of balloon inflation from noise and physiologic effects, such as the occurrence of the dicrotic notch. It will be appreciated, however, that adding too much dither to the inflation timing could have the undesirable effect of causing point A to coincide with or otherwise visually interfere with the occurrence of end diastole. Accordingly, the amount of dither should be limited to avoid such interference.

At step 126, a determination is made as to whether assist duration counter z is greater than one. That is, a reliable APD for cycles 1-4 can be determined if at least two of the cycles had an assist duration of at least 72 msec. If counter z is not greater than one, the process proceeds to step 127 at which sequential failure counter j is incremented by one. It will be appreciated, of course, that the process could require that at least one of the cycles have an assist duration of at least 72 msec, or that three or all of the cycles have the minimum assist duration.

If, on the other hand, assist duration counter z is greater than one in step 126, the process proceeds to step 130. At step 130, an ensemble average of the blood pressure data collected during cycles 1-4 is obtained. As used herein, the term "ensemble average" refers to methods of adding the collected data together on a time-aligned point by point basis and then dividing by the number of data at each point, in this case four. The process of obtaining an ensemble average has the effect of suppressing the substantially random background noise and enhancing the correlated pressure data. The resultant average blood pressure waveform should exhibit a single pressure trough at a measured time from the commencement of data acquisition (i.e., from the time-aligned point at which the inflation command was issued). The pressure trough represents the time at which the effects of balloon inflation are first realized on the blood pressure waveform, that is, point A in FIG. 6. Using bend point analysis techniques, the time location of the pressure trough relative to the time-aligned point at which the inflation command was issued is determined at step 132. Various bend point analysis techniques for finding a peak or a minimum of a curve are known in the art and may be used to find the location of the pressure trough for purposes of the process described herein.

From step 132, the process advances to step 134 at which a determination is made as to whether a trough has been identified and whether it represents the effects of balloon inflation on aortic pressure. If a proper trough is not validated, the process proceeds to step 127 at which sequential failure counter j is incremented by one. If a proper trough is validated in step 134, the process proceeds to step 136 at which sequential counter j is reset to zero. The process then advances to step 138.

The time location determined in step 132 represents an average delay between the inflation command and the time at which the effects of balloon inflation are first realized. As noted previously, this delay is the sum of the intrinsic electro-pneumatic delay and the APD. Since the electro-pneumatic delay is considered a constant of about 28 msec, step 138 subtracts this amount from the average delay determined in step 132 to yield $APD_p$, where p is the number of the APD determination process being run (and is the same number as counter p). Since this is the first APD determination, p equals one and the result obtained is $APD_1$.

In order to assure the accuracy of the APD determined from the foregoing process, the process may be repeated and the results compared. Thus, from step 138 the process may advance to step 140 to determine if p is equal to two. If p is not equal to two, the process proceeds to step 142 at which p is incremented by one. Subsequently, the process proceeds to step 144 in which standard IABP assist is run for a period of about 30 seconds. From step 144, the process returns to step 102 and the entire process for determining the APD is repeated to obtain $APD_2$.

Figure 5A:
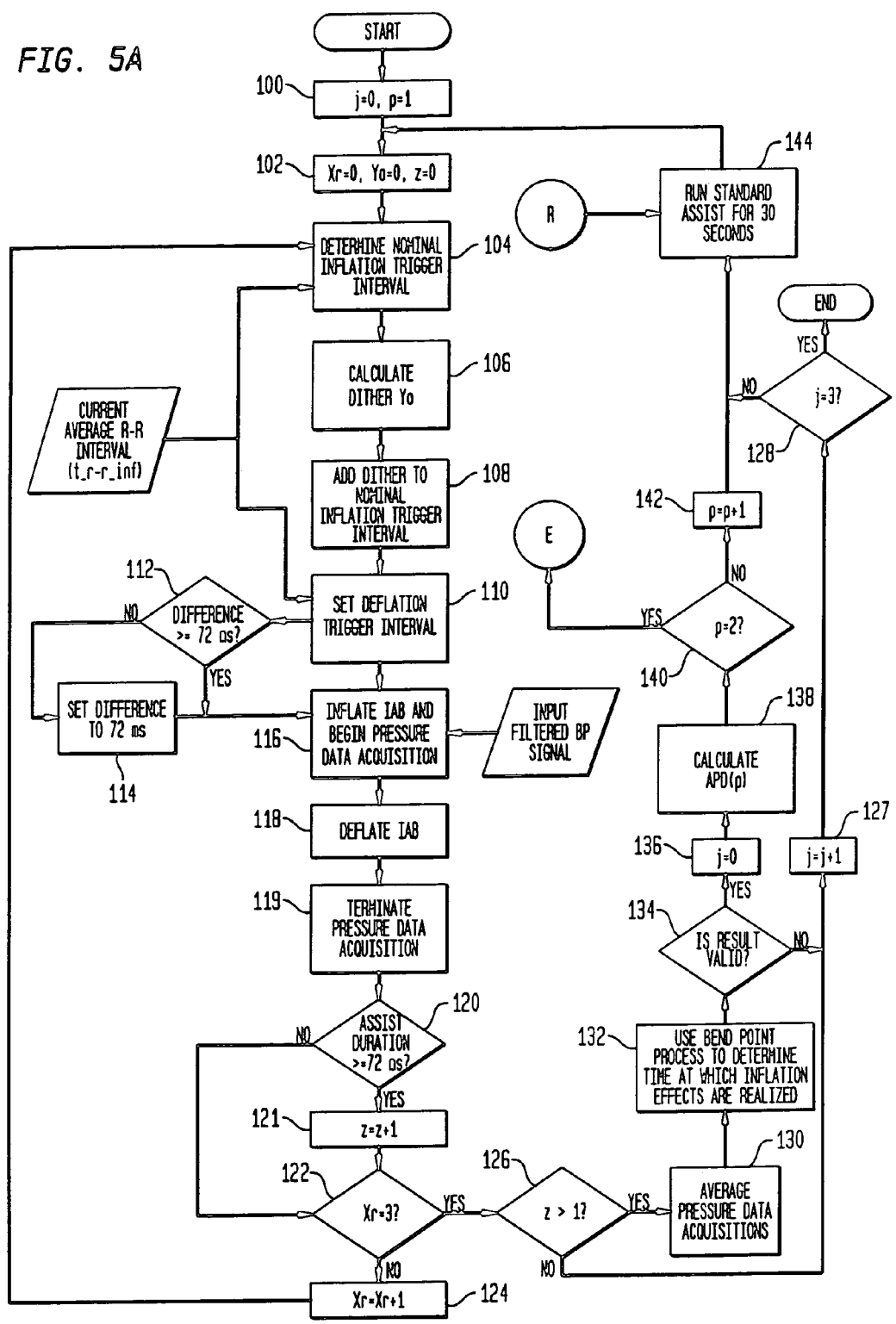
FIGS. 5A and 5B are a flowchart showing the process of the present invention for determining the APD for a particular IABP therapy session where an ECG trigger is used.
Figure 5B:
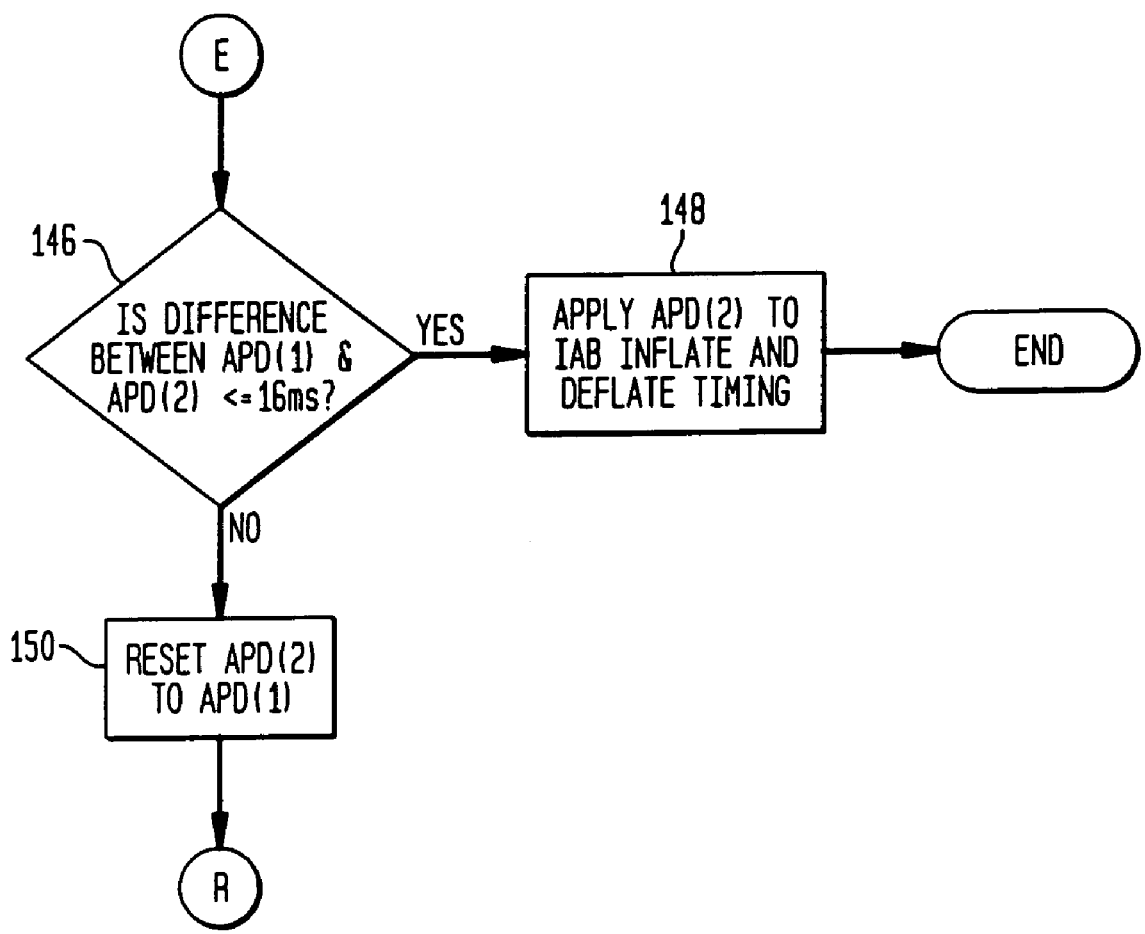

If in step 140 p is equal to two, the process proceeds to step 146, shown in FIG. 5B, in which the APD determined in the first process ($APD_1$) is compared to the APD determined in the second process ($APD_2$). If the difference between the two APD results is less than or equal to 16 msec, the APD determination process is validated, and the balloon inflation and deflation timing is adjusted by $APD_2$ at step 148. The APD determination process is then terminated. It will be appreciated, of course, that a value greater than or less than 16 msec may be used as a threshold value, depending on how close the APD determinations are desired to be. It will also be appreciated that rather than adjust both inflation and deflation timing by the APD, either inflation timing only or deflation timing only may be adjusted by the APD as desired.

If, on the other hand, the difference in the two APD values is greater than 16 msec or another threshold value, the APD determination process is not validated, and the process advances to step 150. At step 150, $APD_2$ is reset as $APD_1$ and the process returns to step 144 in which standard IABP assist is resumed for a period of about 30 seconds. Subsequently, the process returns to step 102 at which counters Xr and z are reset to zero, and the dither amount Yo is reset to zero. However, as counter p is not reset (it remains two), the APD determined in this iteration will be $APD_2$ and will be compared in step 146 to the APD determined in the immediately preceding iteration. Of course, a comparison may be made of three or more APD values as desired.

The overall APD determination process may limit the number of failed attempts at obtaining the APD before it gives up. Failed attempts may result if too many inflation cycles did not provide assist for at least 72 msec or another threshold value, or if a proper pressure trough representing the effects of balloon inflation could not be validated. For example, the process may limit these failed attempts to a total of three consecutive trials. If the APD determination process fails for either of these reasons over three consecutive trials, attempts to obtain a validated APD may be terminated. In such event, the IABP system may run in its semi-automatic mode, wherein the operator manually adjusts the inflation and deflation timing. As noted previously, in this operational mode, the operator implicitly compensates for the APD while setting timing.

Thus, returning to the flowchart of FIG. 5A, each time the sequential failure counter j is incremented in step 127, the process advances to step 128 and a determination is made as to whether three consecutive APD determination trials have failed. If the answer is yes, no further attempts are made to acquire the APD and the process is terminated. However, if the process has not experienced three consecutive failures, standard IABP assist is run for a period of about 30 seconds at step 144, and the process returns to step 102 at which the entire process for determining the APD is repeated. Of course, failed attempts may be limited to a number greater than or less than three consecutive trials, or may require that the failures aggregate to a certain number, but not necessarily be consecutive.

While the foregoing describes a process for determining the APD when an ECG trigger is used, there are situations where the ECG is not available or is corrupted by noise so that R-R intervals are not available. For example, certain surgical procedures employ a current conducting scalpel to cauterize blood vessels as an incision is made to thereby minimize bleeding. The electrical current in the scalpel causes excessive noise in the ECG waveform such that the R-R interval cannot be accurately determined. In such situations, a blood pressure trigger may be used in which balloon inflation is triggered by events occurring on the aortic blood pressure waveform which is not subject to electrical interference.

The method described above for determining the APD may be applied to situations in which a blood pressure trigger is used. Techniques for determining a trigger point based entirely upon blood pressure signals are known in the art and therefore are not described in detail herein. Also known are techniques for determining nominal inflation and deflation command times based on the trigger point. With knowledge of these values, various amounts of dither may be applied to a series of inflation and deflation cycles as described above. The collected data may then be subjected to ensemble averaging to determine the time interval between the inflation command and the point on the pressure waveform at which the effects of balloon inflation are first realized. This time interval may be used to determine and validate the APD using the process described above.

Several variants of the processes described above are contemplated herein. Many of these variants relate to the dithering process. In one such variant, rather than have the dither for successive inflation/deflation cycles steadily increase by $\frac{1}{16}$ of the previous average R-R interval, any succession of dither intervals are possible so long as each dither interval is different from all the preceding intervals. Thus, the dither interval for the initial cycle can be set at $\frac{3}{16} * t_{r\text{-}r\_inf\_avg}$, with each successive inflation/deflation cycle being decreased by $\frac{1}{16}$ of the previous average R-R interval. Alternatively, the dither intervals for successive inflation/deflation cycles can be arranged in no particular order. Regardless of the order in which the dither intervals are added to the nominal inflation trigger interval, the resultant data points should be about the same as should the ensemble average of the data.

In another variant, the dither intervals do not have to be changed on successive heartbeats, but can be changed on every other heartbeat, every third heartbeat, etc. Altering the dither interval on successive heartbeats is preferred, however, because it enables the APD to be determined and applied to the inflation and/or deflation timing more rapidly. Furthermore, dithering over four inflation/deflation cycles is not critical. In that regard, the dithering process should be performed over a sufficient number of cycles to obtain a reliable location for the pressure trough in a reasonable amount of time using ensemble averaging. Accordingly, although dithering over four inflation/deflation cycles is preferred, dithering over a greater or lesser number of cycles is contemplated herein.

In still another variant, the amount of dither added to each inflation/deflation cycle can be different from $\frac{1}{16} * t_{r\text{-}r\_inf\_avg}$. Further, the dither intervals need not be uniform in size, but can vary from one cycle to the next. However, the dither interval preferably is selected so that balloon inflation for that cycle will occur during diastole, and balloon deflation for that cycle will occur prior to the onset of systole.

In a further variant, the amount of dither need not be based on an average of the R-R interval over a predetermined number of preceding heartbeats. Thus, there may be certain situations in which the dither interval is based on the R-R interval of the single immediately preceding heartbeat.

Other variants relate to the method of obtaining an ensemble average of the collected data. In that regard, any method in which the collected data is averaged on a time-aligned point by point basis may be used to obtain an ensemble average.

Figure 9:
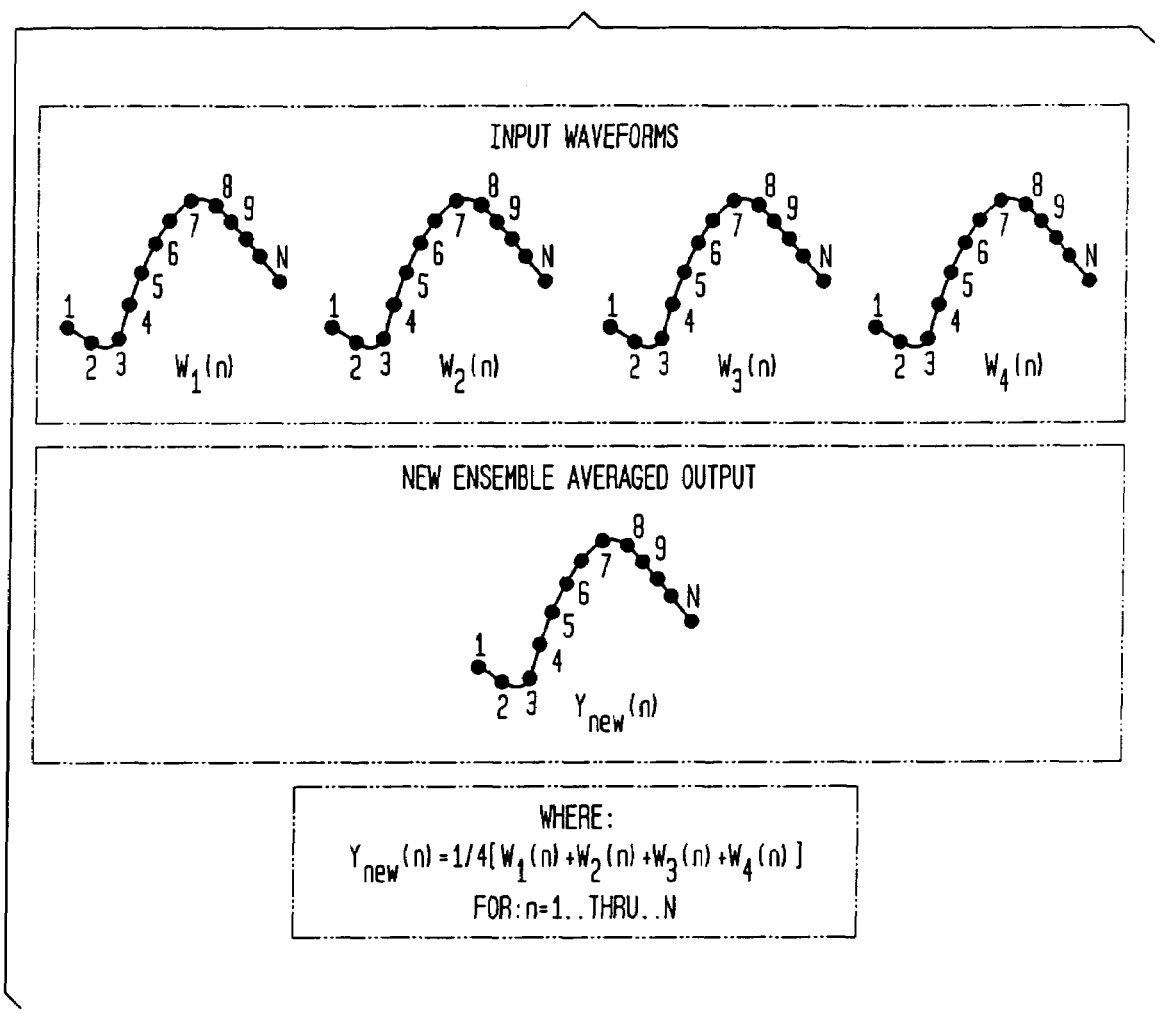
FIG. 9 is a highly schematic diagram illustrating one method of obtaining an ensemble average of the collected pressure data.

One method for determining the ensemble average is similar to the effect of a non-recursive filter. In this method, illustrated in FIG. 9, the time-aligned data points for each cycle of data collection are added together on a point by point basis and divided by the number of cycles according to the formula:

$$Y_{new}(n)=\frac{1}{4}[W_1(n)+W_2(n)+W_3(n)+W_4(n)]$$

where:
$Y_{new}(n)$ is the new ensemble average for the nth data point;
n is the number of the data point collected from one through the total number of data points collected; and
$W_1$ is the first data collection cycle, $W_2$ is the second data collection cycle, etc.

For example, the first data point after issuance of the inflate command for each cycle of data collection are added together and divided by the four cycles of data collection to yield an average value for the first data point. Each subsequent data point is averaged in the same way to yield a resultant curve representing an ensemble average of the collected data. Using bend point analysis, the time location of the pressure trough of this curve is identified and then used to determine APD.

Figure 10:
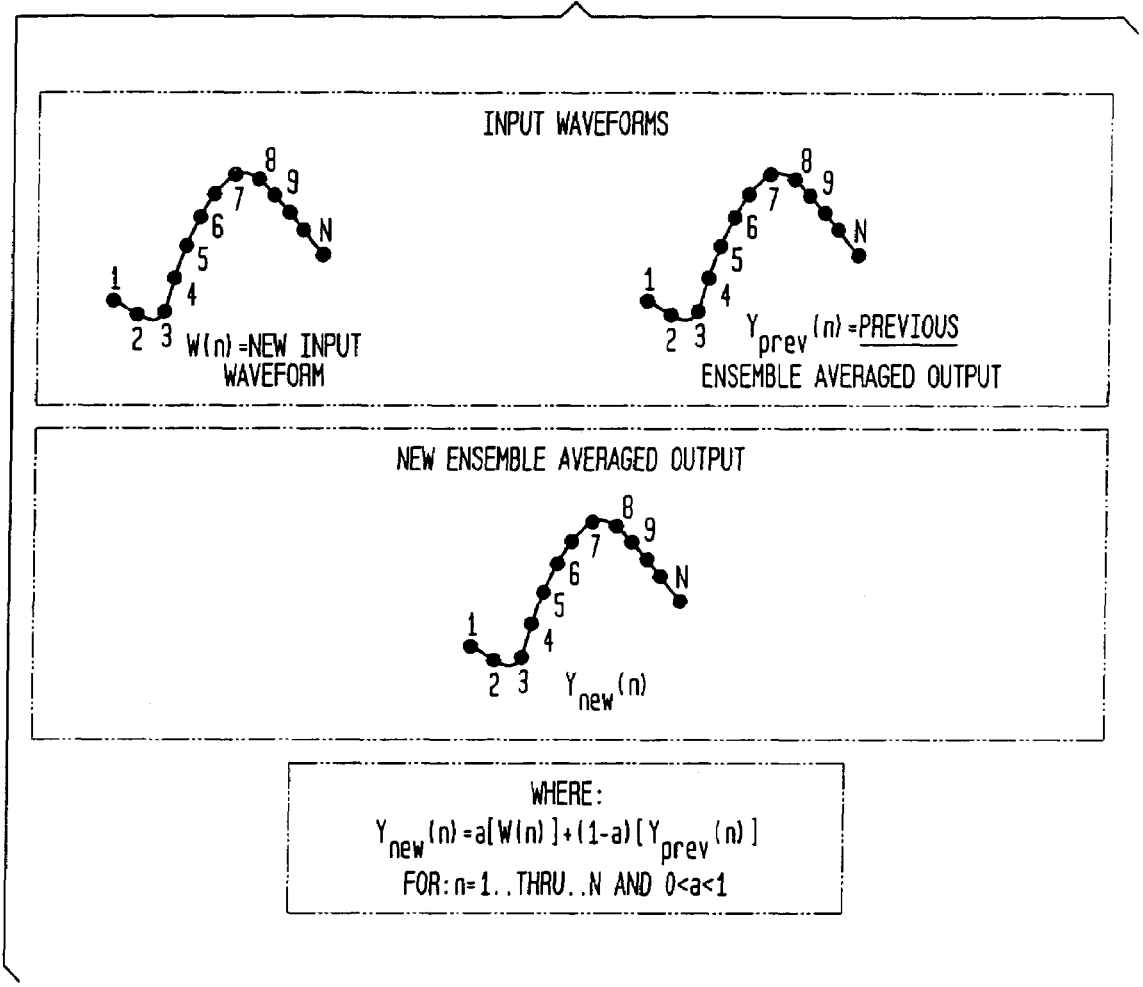
FIG. 10 is a highly schematic diagram illustrating another method of obtaining an ensemble average of the collected pressure data.

Another method for determining the ensemble average is similar to the effect of a recursive filter. In this method, illustrated in FIG. 10, the preceding calculation of the ensemble average is stored in a memory. Then, each data point for a new data collection cycle is added in a weighted fashion to the stored ensemble average to yield a new ensemble average according to the formula:

$$Y_{new}(n)=a[W(n)]+(1-a)[Y_{prev}(n)]$$

where:
$Y_{new}(n)$ is the new ensemble average for the nth data point;
$Y_{prev}(n)$ is the previous ensemble average for the nth data point;
n is the number of the data point collected from one through the total number of data points collected; and
a is a number between 0 and 1 which applies a relative weighting factor to the value of the previous ensemble average and to the current data point.

This formula is applied to the data in each of the data collection cycles, in each case using the newly calculated $Y_{new}(n)$ as $Y_{prev}(n)$ for the next data collection cycle. After the series of data collection cycles has been completed, the resultant curve is analyzed using bend point techniques to identify the time location of the pressure trough of the curve which is then used in the determination of the APD.

In still another method of determining the ensemble average, rather than determining the time location of the pressure trough of the average blood pressure waveform as described above using the recursive or nonrecursive techniques, the process may analyze the data for each of cycles 1-4 to locate the pressure trough for each set of data. The locations of these four pressure troughs relative to the time at which the inflation command for each cycle was issued may then be averaged together to obtain an average time interval from the issuance of the inflation command to the time at which the effects of balloon inflation are first realized on the blood pressure waveform. This average time interval may then be used in the determination of the APD.

The APD determination process need not be run only during startup of IABP therapy. In one preferred arrangement, the process also may be run at predetermined intervals, such as, for example, every 10 minutes. In such arrangement, a newly acquired and validated APD may be compared with the APD currently being applied to balloon inflation. If the difference between the two APDs is less than or equal to 16 msec or some other threshold, the newly acquired APD may be applied to subsequent balloon inflation and deflation timing. If the difference between the two APDs is greater than or equal to the threshold value, the APD determination process may be repeated a selected number of times until the difference between two consecutive APD determinations is less than the threshold value. If that result is not obtainable, that is, if the APD cannot be validated, the timing of subsequent balloon inflation and deflation cycles may not be adjusted by the APD.

In addition to, or rather than, the determination of the APD at regular intervals, the APD process may be initiated manually by an operator. An operator may desire to run the APD process in the event the blood pressure monitoring source were to change, such as when a clinician switches from central lumen monitoring to radial monitoring. The operator may also desire to run the APD process if there is a dramatic change in the patient's blood pressure curve, such as when no augmentation hump is visible in an R-R interval.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as set forth in the appended claims.

The invention claimed is:

1. A method of determining time delays in an intra-aortic balloon pump system between the occurrence of a blood pressure in a patient at a point in time and the display of a pressure value corresponding to the blood pressure in the patient at the point in time on a blood pressure waveform, the intra-aortic balloon pump system including an inflatable chamber, the method comprising:
(a) determining a nominal time to issue an inflate command for inflating the inflatable chamber based on an ECG waveform of the patient's heartbeat;
(b) adding a dither time interval to the nominal inflate command time to obtain an actual inflate command time;
(c) determining a time to issue a deflate command for deflating the inflatable chamber based on the blood pressure waveform;
(d) processing an inflation/deflation cycle in which the inflatable chamber is inflated at the actual inflate command time and deflated at the deflate command time;
(e) acquiring blood pressure data from the patient during the inflation/deflation cycle;
(f) analyzing the acquired blood pressure data to determine a realization time at which the effects of inflating the inflatable chamber are realized on the blood pressure waveform; and
(g) determining a delay time between the actual inflate command time and the realization time.

2. The method as claimed in claim 1, wherein, for a selected heartbeat, the dither time interval is based upon an average of the R-R interval over a predetermined number of the patient's heartbeats immediately preceding the selected heartbeat.

3. The method as claimed in claim 1, wherein, for a selected heartbeat, the dither time interval is proportional to an average of the R-R interval over a predetermined number of the patient's heartbeats immediately preceding the selected heartbeat.

4. The method as claimed in claim 1, further comprising: determining a duration interval between the actual inflate command time and the deflate command time, and if the duration interval is less than a predetermined time interval, adjusting the deflate command time so that the duration interval is at least as large as the predetermined time interval.

5. The method as claimed in claim 1, further comprising: repeating steps (a)-(e) for a plurality of inflation/deflation cycles, in each inflation/deflation cycle the dither time interval added to the nominal inflate command time being different from the dither time interval added to the nominal inflate command time in other inflation/deflation cycles, wherein the analyzing step includes averaging the blood pressure data acquired during the plurality of inflation/deflation cycles on a time-aligned point by point time basis to obtain an ensemble average, and analyzing the ensemble average to determine an average realization time at which the effects of inflating the inflatable chamber are realized on the blood pressure waveform, and the step of determining the delay time includes determining a time-aligned inflate command time based on the actual inflate command time for each of the inflation/deflation cycles and determining a time interval between the time-aligned inflate command time and the average realization time.

6. The method as claimed in claim 5, wherein, for each inflation/deflation cycle, the dither time interval added to the nominal inflate command time is greater than the dither time interval added to the nominal inflate command time in an immediately preceding inflation/deflation cycle.

7. The method as claimed in claim 1, wherein, for a selected heartbeat, the step of determining the nominal inflate command time includes:
determining a Q-$S_2$ time interval between the Q point of the selected heartbeat on the ECG waveform and the $S_2$ point of the selected heartbeat on the blood pressure waveform based on the R-R interval of a heartbeat immediately preceding the selected heartbeat;
determining an inflation trigger time based on the Q point of the selected heartbeat;
determining an inflation trigger delay time between the Q point of the selected heartbeat and the inflation trigger time;
adding the inflation trigger delay time to an electropneumatic delay time to yield a constant delay time;
subtracting the constant delay time from the Q-$S_2$ time interval to yield a start time,
whereby the nominal inflate command time is a time subsequent to the inflation trigger time by the start time.

8. An apparatus for assisting the cardiac function of a patient, comprising:
an inflatable chamber operably positionable with respect to an aorta of the patient;
a catheter connectable in fluid communication with the inflatable chamber;
a drive unit connectable to the catheter for selectively inflating and deflating the inflatable chamber in accordance with a control program; and
a processor for executing the control program;
the control program including a process of determining time delays in the apparatus between the occurrence of a blood pressure in the patient at a point in time and the display of a pressure value corresponding to the blood pressure in the patient at the point in time on a blood pressure waveform, the process including:
(a) determining a nominal time to issue an inflate command for inflating the inflatable chamber based on an ECG waveform of the patient's heartbeat;
(b) adding a dither time interval to the nominal inflate command time to obtain an actual inflate command time;
(c) determining a time to issue a deflate command for deflating the inflatable chamber based on the blood pressure waveform;
(d) processing an inflation/deflation cycle in which the inflatable chamber is inflated at the actual inflate command time and deflated at the deflate command time;
(e) acquiring blood pressure data from the patient during the inflation/deflation cycle;
(f) analyzing the acquired blood pressure data to determine a realization time at which the effects of inflating the inflatable chamber are realized on the blood pressure waveform; and
(g) determining a delay time between the actual inflate command time and the realization time.

9. The apparatus as claimed in claim 8, wherein the process of determining time delays in the apparatus further includes:
repeating steps (a)-(e) for a plurality of inflation/deflation cycles, in each inflation/deflation cycle the dither time interval added to the nominal inflate command time being different from the dither time interval added to the nominal inflate command time in other inflation/deflation cycles, wherein the analyzing step includes averaging the blood pressure data acquired during the plurality of inflation/deflation cycles on a time-aligned point by point time basis to obtain an ensemble average, and analyzing the ensemble average to determine an average realization time at which the effects of inflating the inflatable chamber are realized on the blood pressure waveform, and the step of determining the delay time includes determining a time-aligned inflate command time based on the actual inflate command time for each of the inflation/deflation cycles and determining a time interval between the time-aligned inflate command time and the average realization time.

10. The apparatus as claimed in claim 9, wherein for each inflation/deflation cycle, the dither time interval added to the nominal inflate command time is greater than the dither time interval added to the nominal inflate command time in an immediately preceding inflation/deflation cycle.

11. The apparatus as claimed in claim 8, wherein, for a selected heartbeat, the dither time interval is based upon an average of the RR interval over a predetermined number of the patient's heartbeats immediately preceding the selected heartbeat.

12. The apparatus as claimed in claim 8, wherein, for a selected heartbeat, the dither time interval is proportional to an average of the R-R interval over a predetermined number of the patient's heartbeats immediately preceding the selected heartbeat.

13. The apparatus as claimed in claim 8, wherein the process of determining time delays in the apparatus further includes:

determining a duration interval between the actual inflate command time and the deflate command time, and if the duration interval is less than a predetermined time interval, adjusting the deflate command time in the inflation/deflation cycle so that the duration interval is at least as large as the predetermined time interval.

14. A method of assisting the cardiac function of a patient, comprising:

(a) inserting an inflatable chamber in a selected position with respect to an aorta of the patient;

(b) determining a nominal time to issue an inflate command for inflating the inflatable chamber based on an ECG waveform of the patient's heartbeat;

(c) adding a dither time interval to the nominal inflate command time to obtain an actual inflate command time;

(d) determining a time to issue a deflate command for deflating the inflatable chamber based on a pressure waveform corresponding to the blood pressure in the patient;

(e) processing an inflation/deflation cycle in which the inflatable chamber is inflated at the actual inflate command time and deflated at the deflate command time;

(f) acquiring blood pressure data from the patient during the inflation/deflation cycle;

(g) analyzing the acquired blood pressure data to determine a realization time at which the effects of inflating the inflatable chamber are realized on the blood pressure waveform;

(h) determining a delay time between the actual inflate command time and the realization time;

(i) adjusting the nominal inflate command time by the delay time to obtain a modified inflate command time; and (j) repeatedly inflating the inflatable chamber at the modified inflate command time and deflating the inflatable chamber at the deflate command time.

15. The method as claimed in claim 14, further comprising:

adjusting the deflate command time by the delay time to obtain a modified deflate command time, wherein the step of repeatedly deflating the inflatable chamber includes repeatedly deflating the inflatable chamber at the modified deflate command time.

16. The method as claimed in claim 14, wherein, for a selected heartbeat, the dither time interval is based upon an average of the R-R interval over a predetermined number of the patient's heartbeats immediately preceding the selected heartbeat.

17. The method as claimed in claim 14, wherein, for a selected heartbeat, the dither time interval is proportional to an average of the R-R interval over a predetermined number of the patient's heartbeats immediately preceding the selected heartbeat.

18. The method as claimed in claim 14, further comprising:

determining a duration interval between the actual inflate command time and the deflate command time, and if the duration interval is less than a predetermined time interval, adjusting the deflate command time in the inflation/deflation cycle so that the duration interval is at least as large as the predetermined time interval.

19. The method as claimed in claim 14, further comprising:

repeating steps (b)-(f) for a plurality of inflation/deflation cycles, in each inflation/deflation cycle the dither time interval added to the nominal inflate command time being different from the dither time interval added to the nominal inflate command time in other inflation/deflation cycles, wherein the analyzing step includes averaging the blood pressure data acquired during the plurality of inflation/deflation cycles on a time-aligned point by point time basis to obtain an ensemble average, and analyzing the ensemble average to determine an average realization time at which the effects of inflating the inflatable chamber are realized on the blood pressure waveform, and the step of determining the delay time includes determining a time-aligned inflate command time based on the actual inflate command time for each of the inflation/deflation cycles and determining a time interval between the time-aligned inflate command time and the average realization time.

20. The method as claimed in claim 19, wherein, for each inflation/deflation cycle, the dither time interval added to the nominal inflate command time is greater than the dither time interval added to the nominal inflate command time in an immediately preceding inflation/deflation cycle.

21. A method of determining time delays in an intra-aortic balloon pump system between the occurrence of a blood pressure in a patient at a point in time and the display of a pressure value corresponding to the blood pressure in the patient at the point in time on a blood pressure waveform, the intra-aortic balloon pump system including an inflatable chamber, the method comprising:

(a) determining a nominal time to issue an inflate command for inflating the inflatable chamber based on the blood pressure waveform of the patient;

(b) adding a dither time interval to the nominal inflate command time to obtain an actual inflate command time;

(c) determining a time to issue a deflate command for deflating the inflatable chamber based on the blood pressure waveform;

(d) processing an inflation/deflation cycle in which the inflatable chamber is inflated at the actual inflate command time and deflated at the deflate command time;

(e) acquiring blood pressure data from the patient during the inflation/deflation cycle;

(f) analyzing the acquired blood pressure data to determine a realization time at which the effects of inflating the inflatable chamber are realized on the blood pressure waveform; and (g) determining a delay time between the actual inflate command time and the realization time.

22. An apparatus for assisting the cardiac function of a patient, comprising:

an inflatable chamber operably positionable with respect to an aorta of the patient;

a catheter connectable in fluid communication with the inflatable chamber;

a drive unit connectable to the catheter for selectively inflating and deflating the inflatable chamber in accordance with a control program; and a processor for executing the control program;

the control program including a process of determining time delays in the apparatus between the occurrence of a blood pressure in the patient at a point in time and the display of a pressure value corresponding to the blood pressure in the patient at the point in time on a blood pressure waveform, the process including:

(a) determining a nominal time to issue an inflate command for inflating the inflatable chamber based on the blood pressure waveform of the patient;

(b) adding a dither time interval to the nominal inflate command time to obtain an actual inflate command time;

(c) determining a time to issue a deflate command for deflating the inflatable chamber based on the blood pressure waveform;

(d) processing an inflation/deflation cycle in which the inflatable chamber is inflated at the actual inflate command time and deflated at the deflate command time;

(e) acquiring blood pressure data from the patient during the inflation/deflation cycle;

(f) analyzing the acquired blood pressure data to determine a realization time at which the effects of inflating the inflatable chamber are realized on the blood pressure waveform; and (g) determining a delay time between the actual inflate command time and the realization time.

23. A method of assisting the cardiac function of a patient, comprising:

(a) inserting an inflatable chamber in a selected position with respect to an aorta of the patient;

(b) determining a nominal time to issue an inflate command for inflating the inflatable chamber based on a pressure waveform corresponding to the blood pressure in the patient;

(c) adding a dither time interval to the nominal inflate command time to obtain an actual inflate command time;

(d) determining a time to issue a deflate command for deflating the inflatable chamber based on the blood pressure waveform;

(e) processing an inflation/deflation cycle in which the inflatable chamber is inflated at the actual inflate command time and deflated at the deflate command time;

(f) acquiring blood pressure data from the aorta of the patient during the inflation/deflation cycle;

(g) analyzing the acquired blood pressure data to determine a realization time at which the effects of inflating the inflatable chamber are realized on the blood pressure waveform;

(h) determining a delay time between the actual inflate command time and the realization time;

(i) adjusting the nominal inflate command time by the delay time to obtain a modified inflate command time; and (j) repeatedly inflating the inflatable chamber at the modified inflate command time and deflating the inflatable chamber at the deflate command time.

* * * * *

UNITED STATES PATENT AND TRADEMARK OFFICE
CERTIFICATE OF CORRECTION

PATENT NO. : 7,250,025 B2  
APPLICATION NO. : 10/928534  
DATED : July 31, 2007  
INVENTOR(S) : Paul Nigroni, Brian Prais and Robert Freamon Page 1 of 1

It is certified that error appears in the above-identified patent and that said Letters Patent is hereby corrected as shown below:

Column 18, line 63, "RR" should read --R-R--.

Signed and Sealed this

Twenty-fourth Day of June, 2008

JON W. DUDAS  
*Director of the United States Patent and Trademark Office*